United States Patent [19]

Cuberes-Altisent et al.

[11] Patent Number: 5,166,205
[45] Date of Patent: Nov. 24, 1992

[54] DERIVATIVES OF 1-DIPHENYLMETHYL PIPERAZINE AND THEIR USE AS ANTIHISTAMINES

[75] Inventors: Maria R. Cuberes-Altisent; Jordi Frigola-Constansa; Juan Pares-Corominas, all of Barcelona, Spain

[73] Assignee: Laboratorios Del Dr. Esteve, S. A., Barcelona, Spain

[21] Appl. No.: 735,431

[22] Filed: Jul. 25, 1991

[30] Foreign Application Priority Data

Jul. 26, 1990 [FR] France .............................. 90 09562

[51] Int. Cl.⁵ .................... A61K 31/495; C07D 403/04
[52] U.S. Cl. .................................... 514/252; 544/231; 544/366; 544/370; 544/371; 544/372; 544/396
[58] Field of Search ............... 544/366, 370, 371, 372; 514/252

[56] References Cited

U.S. PATENT DOCUMENTS

| | | | |
|---|---|---|---|
| 3,491,098 | 1/1970 | Archer | 544/370 |
| 3,631,043 | 12/1971 | Regnier et al. | 544/366 |
| 4,338,453 | 7/1982 | Gall | 544/366 |
| 4,377,578 | 3/1983 | Vandenberk et al. | 544/370 |
| 4,525,358 | 6/1985 | Baltes et al. | 514/255 |
| 4,908,365 | 3/1990 | Buzas et al. | 544/370 |
| 5,043,447 | 8/1991 | Pascal et al. | 544/370 |

FOREIGN PATENT DOCUMENTS 0058146 8/1982 France .

OTHER PUBLICATIONS

Gubert et al., "Synthesis of some N-benzhydrylpiperazine drivatives as calcium antagonists," Arzneimittel Forchung, 37(10):1103-1107 (1987).
Boti, J. A. et al., Chemical Abstracts 106(3):614 (1987), Abstract Number 18620u.
Gomez et al., Chemical Abstracts 107(1):668 (1987), Abstract Number 7214j.
Alcaloides, Chemical Abstracts 108(15):763 (1988), Abstract Number 131862d.
Kon et al., Chemical Abstracts 113(17):767 (1990), Abstract Number 152278m.
Hazato et al., Chemical Abstracts, vol. 114, No. 142900 (1991)(Abstract for WO 90 12001 Oct. 18, 1990).
Morren et al., Bull. Soc. Chim. Belg. 60, p. 282 (1951).
de Meglio et al., Farmaco, Ed. Sci., 42, pp. 359-382 (1987).
Baltzly et al., J. Org. Chem. 14, p. 775 (1949).

Primary Examiner—Mukund J. Shah
Assistant Examiner—E. Bernhardt
Attorney, Agent, or Firm—Dressler, Goldsmith, Shore, Sutker & Milnamow, Ltd.

[57] ABSTRACT

The present invention relates to novel derivatives of 1-diphenylmethyl piperazinyl, characterized in that they correspond to the general formula I, and their therapeutically acceptable salts,

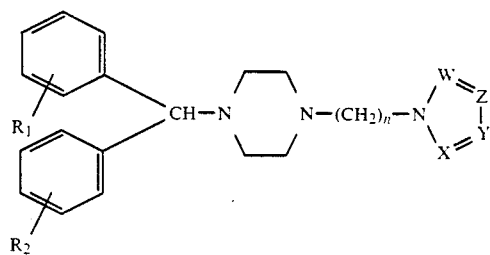

in which:
 $R_1$ and $R_2$, equal or different, represent a hydrogen atom, a halogen, a lower alkyl radical, a hydroxy radical, an alkoxy radical, an alkyl carboxylate radical, an aryl or substituted aryl radical,
 n may have the values 2 to 4,
 X, Y, Z and W, equal or different, represent a nitrogen atom or a carbon atom linked to a hydrogen atom, a halogen or to another alkyl, aryl, carboxyalkyl, carbonyl, hydroxyl, sulfonyl and alkylsulfonyl radical.

The present invention also relates to the process of preparing these compounds and their use for the manufacture of medicaments intended for prophylaxis and for the treatment of various allergic disorders caused by histamine.

5 Claims, No Drawings

DERIVATIVES OF 1-DIPHENYLMETHYL PIPERAZINE AND THEIR USE AS ANTIHISTAMINES

BACKGROUND OF THE INVENTION

The present invention relates to novel derivatives 1-diphenylmethyl piperazine, their process of preparation as well as their use as medicaments.

The compounds according to the present invention correspond to the general formula I

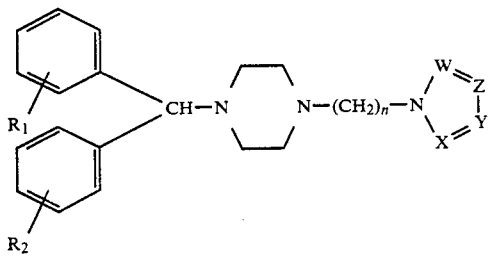

in which:

$R_1$ and $R_2$, equal or different, represent a hydrogen atom, a halogen, a lower alkyl radical, a hydroxy radical, an alkoxy radical, an alkyl carboxylate radical, an aryl radical or substituted aryl radical, n can have the values 2 to 4, X, Y, Z, and W, equal or different, represent a nitrogen atom or a carbon atom linked to a hydrogen atom, a halogen or to another alkyl, aryl, carboxylalkyl, carboxy, hydroxyl, sulfonyl and alkylsulfonyl radical.

These novel derivatives, and their pharmaceutically acceptable salts, show very good antihistaminic activity.

In the scientific literature there have already been known, for a long time, derivatives of diphenylmethyl piperazine with antihistaminic activity, like chlorciclicine (Baltzly and al., J. Org. Chem., 14, 775, 1949); meclicine (Bull. Soc. Chimie Belge., 60, 282, 1951). cetyrizine (EP 58146). However, in general, the usual antihistamines show side effects of stimulation or of depression of the central nervous system. On the other hand, we have discovered that derivatives of the general formula I, and their pharmaceutically acceptable salts, do not show side effects on the central nervous system.

The novel deritives of general formula I may be prepared, according to the invention, according to any one of the following methods:

Method A—By reaction of a compound of general formula

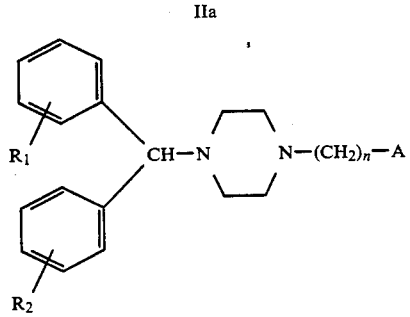

or IIb

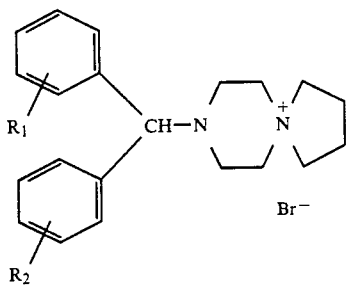

in which $R_1$, $R_2$, and n have the previously mentioned meanings, and A represents a halogen atom, or a good "starting group" selected from among tosyloxy or mesyloxy, with a compound of general formula III

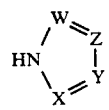

in which X, Y, Z, and W have the previously mentioned meanings.

The reaction is conducted in the presence of a suitable solvent, for example dimethylsulfoxide, dimethylformanide, alcohol, hydrocarbons, aromatic or not, ethers, such as dioxan or diphenyl ether, or mixtures of these solvents. This reaction is avantageously performed in the presence of a base such as hydroxides, carbonates or bicarbonates of alkali metals, or of a mixture of these bases. It is possible to employ also hydrides of alkali metals. The most suitable temperatures vary between room temperature and the reflux temperature of the solvent, and the reaction time is comprised between 1 hour and 24 hours.

Method B—By reaction of a compound of general formula IIa, in which A represents a —NH$_2$ radical, with 2.5-dimethoxytetrahydrofuran.

The reaction is conducted in the presence of a suitable solvent, for example acetic acid, a water, alcohols, ketones or mixtures of these solvents. The most suitable temperatures vary between room temperature and the reflux temperature of the solvent, and the reaction time is comprised of some minutes and 24 hours.

Method C—By reaction of a compound of general formula IV

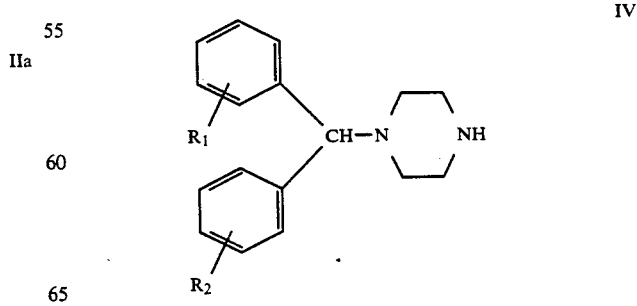

in which $R_1$, $R_2$ have the previously mentioned meanings, with a compound of general formula V

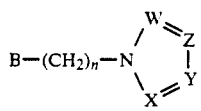

where X, Y, Z, W and n have the previously mentioned meanings and B represents a halogen atom, or a good "starting group" selected from among tosyloxy or mesyloxy.

The reaction is carried out in the presence of a suitable solvent, for example dimethylsulfoxide, dimethylformamide, alcohols, hydrocarbons, aromatic or not, ethers, such as dioxan or diphenyl ether, or mixtures of these solvents. This reaction is advantageously conducted in the presence of a base such as hydroxide, carbonates or bicarbonates of alkali metals, or of a mixture of these bases. The most suitable temperatures vary between room temperature and the reflux temperature of the solvent, and the reaction time is comprised between 1 hour and 24 hours.

In the following examples, the preparation of the novel derivatives according to the invention is indicated. The following examples, given purely by way of illustration, must not however, in any case, be taken as limiting the scope of the invention.

DESCRIPTION OF PREFERRED EMBODIMENTS

Method A

EXAMPLE 1

Preparation of 4-Bromo-1-[4-(4-diphenylmethyl piperazinyl)butyl]pyrazole.

a) 8-aza-5-azoniaspiro [4,5] decane-8-diphenylmethyl bromide.

Under reflux for 16 hours a mixture of 10 g (39.7 mmoles) of 1-diphenylmethyl piperazine, 11.9 g (55.1 mmoles) of 1,4-dibromobutane and 5.5 g (39.7 mmoles) of potassium carbonate were heated in 60 ml of chloroform. It was cooled, filtered and evaporated. The residue was triturated in ethyl ether and 15.1 g of solid was obtained, with a melting point 256°–262° C. $^1$H-NMR (CDCl$_3$): 2.2 (m,4H); 2.7 (m,8H); 4.35 (s,1H); 7.2 (m,10H).

b) 4-Bromo-1-[4-(4-diphenylmethyl-1-piperazinyl)-butyl]pyrazole.

Under reflux for 19 hours, a mixture of 5 g (12.9 mmoles) of 8-asa-5-azoniaspiro [4.5] decane-8-diphenyl-methyl bromide, 2.2 g (14.9 mmoles) of 4-bromo-1-H-pyrazole, and 2.74 g (19.9 mmoles) of potassium carbonate in 50 ml of dimethylformamide were heated. It was cooled, and it was filtered and the filtrate evaporated to dryness. The residue was taken up again with chloroform and washed with water. The organic phase which dried with Na$_2$SO$_4$, it was filtered and evaporated. The product was obtained in the form of a crude oil, its hydrochloride was prepared with hydrochloric methanol and it was crystallized in ethanol-ethyl ether. 5.5 g of the corresponding hydrochloride was obtained, with a melting point 184°–189° C.

The spectroscopic data for its identification are given in Tables 1 and 2.

EXAMPLE 2

Preparation of 4-Chloro-1-[4-(-4-diphenylmethyl-1-piperazinyl)butyl]pyrazole.

The preparation is carried out with the same method as that shown in example 1a and 1b.

The hydrochloric acid salt is prepared in ethanol-ethyl ether, with a melting point 173°–176° C.

The spectroscopic data for its identification are shown in tables 1 and 2.

EXAMPLE 3

Preparation of 4-Bromo-1-[3-(4-diphenyl-methyl-1-piperazinyl)propyl]pyrazole. a) 1-(3-chloropropyl)-4-diphenylmethyl piperazine.

Under reflux for 16 hours a mixture of 5 g (19.8 mmoles) of 1-diphenylmethyl piperazine, 3.75 g (23.8 mmoles) of 1-bromo-3-chloropropane and 3.3 g (24 mmoles) of potassium carbonate were placed in 100 ml of chloroform. It was cooled, filtered and the filtrate evaporated to dryness. The crude residue obtained was purified on a chromatographic silica column (eluant: ethyl acetate) and in this way 1.24 g of 1-(3-chloropropyl)-4-diphenylmethyl piperazine was obtained.

$^1$H-NMR (CDCl$_3$): 1.9 (m,2H); 2.35 (m,10H); 3.45 (t,2H); 4.15 (s,1H); 7.2 (m,10H)

b) 4-Bromo-1-[3-(4-diphenylmethyl-1-piperazinyl)-propyl]pyrazole.

The preparation was carried out with a procedure parallel with that shown in example 1b.

The product was purified on a chromatographic silica column (eluant: chloroform-methanol 95:5). Its hydrochloride in hydrochloric ethanol was prepared, which had a melting point of 106°–110° C.

The spectroscopic data for its identification are shown in Tables 1 and 2.

EXAMPLE 4

Preparation of 1-[4-(Diphenylmethyl-1-piperazinyl)-butyl]-4-carboxy pyrazole.

The preparation was carried out with a procedure parallel to that explained in examples 1a and 1b, and 1-[4-(4-Diphenylmethyl-1-piperazinyl)butyl]-4-ethyloxy-carbonylpyrazole was obtained with a melting point of 70°–75° C.

$^1$H-NMR (CDCl$_3$): 1.31 (t,3H); 1.48 (m,2H); 1.86 (m,2H); 2.41 (m,10H); 4.08 (t,2H); 4.20 (s,1H); 4.30 (t,2H); 7.12–7.46 (m,10H); 7.87 (d,2H). IR (KBr): 1708, 1552, 1237, 1152, 773, 706 cm$^{-1}$

The previously prepared ester was hydrolyzed by treatment of a solution in ethanol, for 15 hours at ambient temperature, with 10% caustic soda. The alcohol was evaporated and the aqueous solution was neutralized with hydrochloric acid. It was extracted with chloroform, it was dried with Na$_2$SO$_4$, filtered and evaporated. In this way the corresponding acid with a melting point of 102°–105° C. was obtained.

Its hydrochloride cristallized in ethanol-ethyl ether, with a melting point of 148°–152° C.

The spectroscopic data for its identification are shown in Tables 1 and 2.

EXAMPLE 5

Preparation of 1-4-[4-(-Diphenylmethyl-1-piperazinyl)butyl]-4-methyl pyrazole.

The preparation was carried out with a procedure similar to that explained in examples 1a and 1b.

The salt with maleic acid was prepared in ethanol-ethyl ether, with a melting point 122°–126° C.

The spectroscopic data for its identification are shown in Tables 1 and 2.

EXAMPLE 6

Preparation of 1-[4-(4-Diphenylmethyl-1-piperazinyl)butyl]imidazole.

The preparation was carried out with a procedure parallel to that explained in examples 1a and 1b. The product was purified on a chromatographic silica column (eluant:chloroform-methanol 95:5) in oil form.

The salt is prepared with maleic acid in ethanol-ethyl acetate, with a melting point 146°–149° C.

The spectroscopic data for its identification are given in Tables 1 and 2.

EXAMPLE 7

Preparation of 1-[4-(4-Diphenylmethyl-1-piperazinyl)butyl]-1,2,4,-triazole.

The preparation is carried out with a procedure similar to that explained in examples 1a and 1b, and it is purified on a chromatographic silica column (eluant:chloroform-methanol 93:7). The derivative is obtained in the form of an oil. Its hydrochloride is prepared and it is crystallized in ethanol-ethyl acetate, with a melting point of 201°–203° C.

The spectroscopic data for its identification are given in Tables 1 and 2.

Method B

EXAMPLE 8

Preparation of 1-[4-(4-Diphenylmethyl-1-piperazinyl)butyl]pyrrole.

Under reflux, for 20 minutes is heated a solution of 1.28 g (3.96 mmoles) of 1-(4-aminobutyl)-4-diphenylmethylpiperazine and 0.77 g (5.8 mmoles) of 2.5-dimethoxytetrahydrofurane in 25 ml of acetic acid. It is cooled, it is poured over ice water, neutralized with $NaCHO_3$ and extracted with chloroform. It is dried with $Na_2SO_4$, and evaporated under vacuum to dryness. 1.7 g of crude oil is obtained which is purified on a silica chromatographic column (eluant: ethyl acetate). 0.95 g of 1-[4-(4-Diphenylmethyl-1-piperazinyl)butyl]pyrrole is obtained in solid form, with a melting point 80°–84° C.

The salt is prepared with maleic acid in ethanol-ethyl ether, with a melting point 136°–140° C.

The spectroscopic data for its identification are shown in Tables 1 and 2.

Method C

EXAMPLE 4

Preparation of 1-[4-(4-Diphenylmethyl-1-piperazinyl)butyl]-4-carboxy pyrazole.

Under reflux for 4 hours is placed a mixture of 6.3 g (25 mmoles) of diphenylmethyl piperazine, 6.87 g (25 mmoles) of 1-(4-bromobutyl)-4-ethyloxycarbonylpyrazole, 5.17 g (37.5 moles) of potassium carbonate and 5.06 g (33.7 mmoles) of sodium iodide in 100 ml of methyl ethyl ketone. It is cooled, filtered and the filtrate evaporated to dryness. The residue is taken up again with chloroform and water, the organic phase is dried with $Na_2SO_4$, it is filtered and evaporated under vacuum. The resulting product is purified on a chromatographic silica column (eluant: chloroform-methanol 95:5) and in this way 7.4 g of 1-[4-(4-Diphenylmethyl-1-piperazinyl)butyl]-4-ethyloxycarbonylpyrazole is obtained, with a melting point 70°–74° C.

The spectroscopic data of the compound are the same as those already shown in example 4 of method A.

This ester is hydrolyzed with a procedure similar to that shown in example 4 of method A and the acid is obtained with the same spectroscopic data shown in Tables 1 and 2.

EXAMPLE 8

Preparation of 1-[4-(4-Diphenylmethyl-1-piperazinyl)butyl]pyrrole.

The preparation is carried out with a procedure similar to that shown in the preceding example. The product is obtained with a melting point of 81°–84° C.

The spectroscopic data of the compound are the same already shown in Tables 1 and 2.

EXAMPLE 9

Preparation of 1-[4-(4-Diphenylmethyl-1-piperazinyl)butyl]pyrazole.

The preparation was carried out with a procedure quite similar to that shown in the preceding example. In this way the product with a melting point 60°–64° C. was obtained.

Its hydrochloride crystallises in ethanol-ethyl ether, with a melting point 160°–165° C.

The spectroscopic data for its identification are shown in Tables 1 and 2.

TABLE I

[Structure: Ar(R1)-CH(Ar-R2)-N(piperazine)N-(CH2)n-N(heterocycle with W=Z, X=Y)]

| Example no | R1 | R2 | n | Heterocycle (–N ring) | Method | IR (cm$^{-1}$) (KBr) |
|---|---|---|---|---|---|---|
| 1 | H | H | 4 | pyrazole-4-Br | A | .HCl 1456, 950, 919, 762, 706 |
| 2 | H | H | 4 | pyrazole-4-Cl | A | .HCl 1487, 1437, 1294, 975, 750, 712 |
| 3 | H | H | 3 | pyrazole-4-Br | A | .HCl 1656, 1456, 950, 756, 706 |
| 4 | H | H | 4 | pyrazole-4-CO$_2$H | A, C | .HCl 1719, 1556, 1430, 1194, 762, 706 |
| 5 | H | H | 4 | pyrazole-4-CH$_3$ | A | maleate: 1694, 1469, 1350, 869, 706, 650 |
| 6 | H | H | 4 | imidazole | A | (film) 1452, 1283, 1151, 1077, 756, 706, 662 |
| 7 | H | H | 4 | 1,2,4-triazole | A | (film) 1505, 1492, 1451, 1273, 1139, 1009, 756, 707 |
| 8 | H | H | 4 | pyrrole | B, C | maleate: 1694, 1469, 1350, 869, 744, 706, 650 |
| 9 | H | H | 4 | pyrazole | C | 1449, 1307, 1283, 1140, 1009, 750, 706 |

TABLE 2

| Example no | $^1$H-NMR (CDCl$_3$) δ |
|---|---|
| 1 | 1.65(m, 4H); 2.20(m, 10H); 3,8(t, 2H); 4.0 (s, 1H); 6.9–7.3(m, 12H) |
| 2 | 1.37(m, 2H); 1.70(m, 2H); 2.33(m, 10H); 3.94 (t, 2H); 4.12(s, 1H); 6.9–7.4(m, 12H) |
| 3 | 1.89(m, 2H); 2.17(t, 2H); 2.32(m, 8H); 4.0 (t, 2H); 4.12(s, 1H); 7.04–7.37(m, 12H) |
| 4 | 1.37(m, 2H); 1.82(m, 2H); 2,39(m, 10H); 4.08 (t, 2H); 4.20(s, 1H); 7.15–7.49(m, 10H); 7.90 |

TABLE 2-continued

| Example no | $^1$H-NMR (CDCl$_3$) δ |
|---|---|
| | (d, 2H) |
| 5 | 1.6(m, 4H); 2.05(s, 3H); 2.35(m, 10H); 3.85 (t, 2H); 4.1(s, 1H); 6.9–7.3(m, 12H) |
| 6 | 1.46(m, 2H); 1.79(m, 2H); 2.40(m, 10H); 3.91 (t, 2H); 4.20(s, 1H); 6,9–7,45(m, 13H) |
| 7 | d$_6$-DMSO: 1.45(m, 2H); 1.80(m, 2H); 2.42(m, 10H); 4.00–4.20(m, 3H); 7.15–7.35(m, 10H); 7.82(s, 1H); 8.25(s, 1H) |
| 8 | 1.50(m, 2H); 1.76(m, 2H); 2.40(m, 10H); 4.09 (t, 2H); 4.19(s, 1H); 6.10(m, 2H); 6.61(m, 2H); 7.00–7.40(m, 10H) |
| 9 | 1.46(m, 2H), 1.86(m, 2H); 2.44(m, 10H); 4.11 (t, 2H); 4.20(s, 1H); 6.20(m, 1H); 7.17–7.47 (m, 12H) |

Pharmacological activity

The products according to the present invention are powerful antihistamines which are characterized by the fact of being free of sedative action, contrary to the majority of known antihistamines.

"In vivo" antihistamine activity

The antihistaminic activity was studied by determining the protection in the face of the mortality used by the product 48/80 in the rat. This test was performed in accordance with the technique described by C. J. E. Niemegeers et cols. (Arch. int. Pharmacodyn., 234, 164-176 (1978). The products according to the present invention are administered intra-peritonially to rats. After 60 minutes the compound 48/80 is administered (0.5 mg/kg, i.v.).

The protective activity is defined as the survival of the rats four hours after the i.v. injection of 48/80.

The activity of the products was studied at several doses in order to determine the dose capable of protecting 50% of the animals (ED-50).

Then, the anti-histaminic activity of some of the products according to the present patent application was summarized. This activity was compared with that of difenhidramine, a reference antihistamine. The majority of the products according to the present invention are more active than difenhidramine, considering that their ED-50 is smaller.

"In vivo" antihistaminic activity Protection from death induced by 48/80

| Example no. | ED-50 (mg/kg, i.p.) |
|---|---|
| 1 | 3.2 |
| 2 | 3.0 |
| 3 | 10 |
| 4 | 0.62 |
| 5 | 0.62 |
| 6 | 2.5 |
| 7 | 0.60 |
| 8 | 6.7 |
| Difenhidramine | 5.4 |

Sedative action: 1) Irwin Test

To study the absence of sedative effect of the products according to the present invention, they were administered to rats intra-peritonially and the behaviour of the animals was observed following the standards described in the test of S Irwin (Science, 136, 123–128 (1962)).

Below are collected the results obtained in the two evaluations which reflect the sedative action:

Pas.: Passivity, sedation, prostation. Quantitative evaluation between 0 and 3. They were performed 1, 2 and 3 hours after the treatment.

Atax.: Ataxia, the alterations of coordination in locomotion were evaluated. They were evaluated between 0 and 3. They were performed 1, 2 and 3 hours after the treatment.

Below are summarized the results of the study of the sedative effect of some of the products according to the present invention, by way of example. This activity was compared to that of difenhidramine, the reference antihistamine. The products according to the present invention showed very slight sedative action, contrary to difenhidramine which is established to be toxic at the dose of 80 mg/kg, i.p., on account of the depresser effects of the CNS.

Sedative action: 1) Irwin Test

| Example no | Dose (mg/kg) | Effect Pas. | Atax. |
|---|---|---|---|
| 1 | (20) | 0.8 | 1.2 |
| | (40) | 0.8 | 1.4 |
| | (80) | Toxic | |
| 2 | (40) | 0.2 | 1.5 |
| | (80) Tox. | 0 | 0.4 |
| 3 | (80) | 0 | 0.7 |
| 4 | (80) | 0.9 | 1 |
| | (160) | 1.2 | 1.6 |
| 5 | (80) | 0.7 | 0.5 |
| 6 | (80) | 1.3 | 0.3 |
| 7 | (80) | Toxic | |
| Difenhidramine | (40) | 0 | 0.9 |
| | (80) | Toxic | |

Sedative effect: 2) Potentiation of the sleep time induced by pentobarbital

The study of the potentiation of the sleep time due to the pentobarbital was performed following the method described by L. E. Allen and cols. (Arz. Forsch. 24, (6), (1974)). The products studied were administered orally. One hour later the sodium pentobarbital (35 mg/kg, s.c.) was administered and the time that the animals are delayed in waking up again was determined. The sleep time was compared with a group of control animals, treated only with sodium pentobarbital.

In order to complete the studies which demonstrate the absence of sedative action of the products according to the present invention, this test was prepared with the activity of one of the most powerful of the products and with a less sedative action (example 5) with the reference antihistamine, difenhidramine. Below are presented the results of this test with example 5 and difenhidramine. It is obvious that difenhidramine potentiates significantly the sleep time at the dose of 20 mg/kg, whilst example 5 does not potentiate the sleep time induced by the pentobarbital except at the dose of 160 mg/kg.

Sedative action: 2) Potentiation of the sleep time induced by pentobarbital

| Example no | Dose (mg/kb p.o.) | Potentiation sleep time | |
|---|---|---|---|
| 5 | 40 | 15% | N.S. |
| | 80 | 21% | N.S. |

| Example no | Dose (mg/kb p.o.) | Potentiation sleep time | |
|---|---|---|---|
| | 160 | 33% | * |
| Difenhidramine | 10 | 22% | N.S. |
| | 20 | 38% | * |

N.S.: Not significant
*Significant difference with the control group (p < 0.05)

There is indicated below, by way of example, a particular galenic form of the derivatives according to the present invention.

| Tablets Formula per tablet | |
|---|---|
| Example no 5 | 10.00 mg |
| Lactose | 54.00 mg |
| Corn starch | 26.00 mg |
| Microcrystaline cellulose | 18.00 mg |
| Polyvinylpyrrolidone | 6.00 mg |
| Sodium croscarmellose | 3.60 mg |
| Colloidal silica dioxide | 0.60 mg |
| Magnesium stearate | 1.20 mg |
| | 120.00 mg |

We claim:

1. Derivatives of 1-diphenylmethyl piperazinyl characterized in that they correspond to the formula I, or their therapeutically acceptable salts,

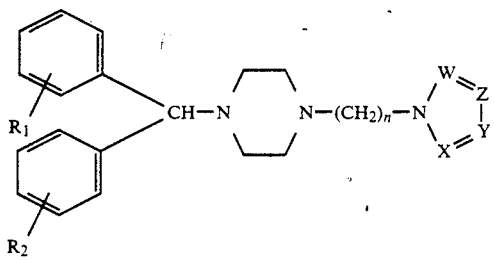

I in which:

$R_1$ and $R_2$, equal or different, represent a hydrogen atom, a halogen, a lower alkyl radical or a hydroxy radical, n may have the values 2 to 4, X, Y, Z, and W, equal or different, represent a nitrogen atom or a carbon atom linked to a hydrogen atom, a halogen or to another lower alkyl carboxy, hydroxyl, or lower alkoxy carbonyl radical.

2. The compounds selected from among the following group:
   4-Bromo-1-[4-(4-diphénylméthyl pipérazinyl)butyl]-pyrazole
   4-Chloro-1-[4-(4-diphénylméthyl-1-pipérazinyl)-butyl]pyrazole
   4-Bromo-1-[3-(4-diphénylméthyl-1-pipérazinyl)-propyl]pyrazole
   1-[4-(4-Diphénylméthyl-1-pipérazinyl)butyl]-4-carboxypyrazole
   1-[4-(4-Diphénylméthyl-1-pipérazinyl)butyl]-4-methylpyrazole
   1-[4-(4-Diphénylméthyl-1-pipérazinyl)butyl]imidazole
   1-[4-(4-Diphénylméthyl-1-pipérazinyl)butyl]-1,2,4-triazole
   1-[4-(4-Diphénylméthyl-1-pipérazinyl)butyl]pyrrole
   1-[4-(4-Diphénylméthyl-1-pipérazinyl)butyl]-4-éthyloxycarbonylpyrazole
   1-[4-(4-Diphénylméthyl-1-pipérazinyl)butyl]-pyrazole.

3. A derivative in accordance with claim 1 wherein one of X, Y, Z and W represents a carbon atom limited to an ethyloxycarbonyl radical.

4. Pharmaceutical compositions, characterized by the fact that they contain, besides a pharmaceutically acceptable support, at least one derivative of formula I or one of its physiologically acceptable salts, according to one of claims 1 or 2.

5. Method for treating, in a patient, various allergic disorders caused by histamine, comprising administrating to said patient an effective dose of at least one of the derivatives of the formula I or its physiologically acceptable salts, according to one of claims 1 or 2.

* * * * *

UNITED STATES PATENT AND TRADEMARK OFFICE
CERTIFICATE OF CORRECTION

PATENT NO. : 5,166,205

DATED : November 24, 1992

INVENTOR(S) : Maria R. Cuberes-Altisent, Jordi Frigola-Constansa, and Juan Pares-Corominas It is certified that error appears in the above-identified patent and that said Letters Patent is hereby corrected as shown below:

Column 12, line 31
Claim 3, line 2, "limited" should be --linked--.

Signed and Sealed this

Sixteenth Day of November, 1993

*Attest:*

BRUCE LEHMAN

*Attesting Officer*   *Commissioner of Patents and Trademarks*